(12) United States Patent
Enderle et al.

(10) Patent No.: US 8,309,310 B2
(45) Date of Patent: Nov. 13, 2012

(54) GENERIC KINASE/PHOSPHATASE ASSAY WITH SINGLE READOUT

(75) Inventors: Thilo Enderle, Rheinfelden (DE); Doris Roth, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 151 days.

(21) Appl. No.: 12/677,127

(22) PCT Filed: Sep. 1, 2008

(86) PCT No.: PCT/EP2008/007122
§ 371 (c)(1), (2), (4) Date: Mar. 9, 2010

(87) PCT Pub. No.: WO2009/033580
PCT Pub. Date: Mar. 19, 2009

(65) Prior Publication Data
US 2010/0203554 A1    Aug. 12, 2010

(30) Foreign Application Priority Data

Sep. 10, 2007 (EP) .................................. 07115987

(51) Int. Cl.
*G01N 33/53* (2006.01)
(52) U.S. Cl. ........................................ 435/7.1; 436/518
(58) Field of Classification Search .................. None
See application file for complete search history.

(56) References Cited

U.S. PATENT DOCUMENTS

| | | | |
|---|---|---|---|
| 7,585,643 B2 * | 9/2009 | Sem | 435/15 |
| 2004/0171034 A1 * | 9/2004 | Agnew et al. | 435/6 |
| 2005/0106655 A1 | 5/2005 | Savage et al. | |
| 2007/0009978 A1 | 1/2007 | Enderle et al. | |
| 2009/0253150 A1 | 10/2009 | Enderle et al. | |

FOREIGN PATENT DOCUMENTS

| | | |
|---|---|---|
| EP | 1674580 | 6/2006 |
| WO | 2006/102129 | 9/2006 |
| WO | 2007/016975 | 2/2007 |

OTHER PUBLICATIONS

Marme et al. (Bioconjugate Chem 2003 vol. 14, p. 1133-1139).*
Sahoo H et al: "Single-label kinase and phosphatase assays for tyrosine phosphorylation using nanosecond time-resolved fluorescence detection". Journal of the American Chemical Society (2007), 129:51 15927-15934, XP002501457.

* cited by examiner

*Primary Examiner* — Jacob Cheu
(74) *Attorney, Agent, or Firm* — George W. Johnston; Dennis P. Tramaloni; Brian C. Remy

(57) ABSTRACT

The present invention relates to a generic method for detecting a kinase or phosphatase activity. The method comprises the following steps: incubating a kinase or phosphatase activity sample with a kinase or phosphatase substrate molecule comprising either a fluorophore having a detectable readout or molecule with an aromatic group which serves as a quencher of the fluorophore, incubating the mixture of step a) with a detection entity comprising either a fluorophore or a molecule with an aromatic group and a binding partner, wherein the substrate molecule and the detection entity are capable of binding to the binding partner and the binding of the substrate molecule and the detection entity to the binding partner lead to an altered readout of the fluorophore, and measuring the readout of the fluorophore in the mixture of step b), wherein an altered readout of the fluorophore compared to a blank is indicative for the presence of a kinase or phosphatase activity in the sample.

22 Claims, 5 Drawing Sheets

GENERIC KINASE/PHOSPHATASE ASSAY WITH SINGLE READOUT

This application is the National Stage of International Application No. PCT/EP2008/007122 filed Sep. 1, 2008, which claims the benefit of EP 07115987.5 filed Sep. 10, 2007, which is hereby incorporated by reference in its entirety.

The present invention is directed to a generic assay for detecting a kinase or phosphatase activity and its use in life science and drug discovery.

During the last years several methods have been developed for the detection of phosphorylation (kinase activity) or dephosphorylation (phosphatase activity) of peptides or proteins for use in in-vitro pharmacology and high throughput screening (HTS). Most attractive for such applications are detection methods with fluorescent readout which are homogeneous, mix-and-measure assays and which are thus suitable for miniaturization. Common assays are based on the binding of a specific antibody to the phosphate group, however antibody based assays are not generic as antibodies for phosphoserine or phosphothreonine are sequence specific. Immobilized metal ion affinity based assays (IMAP) are antibody free and thus generic. Another generic assay for the detection of kinase activity is the Transcreener assay where the production of ADP is measured. In all these assays the detection of kinase/phosphatase activity is based on fluorescence polarization (FP) or fluorescence resonance energy transfer (FRET, TR-FRET, HTRF).

These fluorescence measurements, however, require multiple readout of different optical parameters such as polarization, wavelengths, time delayed detection which requires a more sophisticated instrumentation than a simple fluorescence intensity measurement. The ADP assay is only suitable for high ATP/ADP concentrations and high turnover of the enzyme and one might easily run out of the linear range of the reaction. Furthermore the detection is only indirect, since the ATP/ADP consumption are monitored which might not be specific and not the (de-)phosphorylation of the specific phosphatase or kinase substrate.

Therefore, there is a need for an improved generic kinase and phosphatase assay allowing an efficient detection of the kinase or phosphatase activity.

It is an object of the present invention to provide a method for detecting a kinase activity or phosphatase activity which fulfills this requirement by a robust and reliable fluorescence readout.

This method comprises the following steps:
a) incubating a kinase or phosphatase activity sample with a kinase or phosphatase substrate molecule comprising a fluorophore having a detectable readout,
b) incubating the mixture of step a) with a detection entity comprising an aromatic group and a binding partner, wherein the phosphorylated substrate molecule and the detection entity are capable of binding to the binding partner and the binding of the substrate molecule and the detection entity to the binding partner lead to an altered readout of the fluorophore, and
c) measuring the readout of the fluorophore in the mixture of step b), wherein an altered readout of the fluorophore compared to a blank is indicative for the presence of a kinase or phosphatase activity in the sample.

In a second object, the present invention is directed to a method for detecting a kinase activity or phosphatase activity. Said method comprises the following steps:
a) incubating a kinase or phosphatase activity sample with a substrate molecule comprising an aromatic group,
b) incubating the mixture of step a) with a detection entity comprising a fluorophore having a detectable readout and a binding partner, wherein the phosphorylated substrate molecule and the detection entity can bind to the binding partner and the binding of the substrate molecule and the detection entity to the binding partner lead to an altered readout of the fluorophore, and
c) measuring the readout of the fluorophore in the mixture of step b), wherein an altered readout of the fluorophore compared to a blank is indicative for the presence of a kinase or phosphatase activity in the sample.

In an embodiment of the present invention, the fluorophore is selected from the group consisting of Fluorescein, Rhodamine B, Tetramethylrodamine, ATTO 590, ATTO 655, ATTO 680, Atto 700, MR 121, Bodipy 630/650 and Bodipy FL. Preferred fluorophores are selected from the group consisting of MR 121, ATTO 590, ATTO 655, Atto 680 and ATTO 700. Particular preferred fluorophores for use in a method of the present invention are MR 121 and Atto 700. The molecular structures of some of these fluorophores can be found in Bioconjugate Chem. 2003, 14, 1133-1139. The ATTO molecules are commercially available from Atto-Tec GmbH, Siegen, Germany.

In another embodiment of the present invention, the aromatic group is selected from the group of amino acids with aromatic systems, preferably tryptophan. Other suitable aromatic groups for use in the method of the present invention are selected from molecules like cGMP or cAMP derivatives.

The substrate molecule is preferably a peptide comprising at least a tyrosine and/or serine and/or threonine.

In another embodiment, the method is for detecting a tyrosine kinase activity and the substrate peptide comprises at least a tyrosine.

In yet another embodiment, the method is for detecting a serine kinase activity and the substrate peptide comprises at least a serine.

In yet another embodiment, the method is for detecting a threonine kinase activity and the substrate peptide comprises at least a threonine.

In a further embodiment, the method is for detecting a phosphatase activity and the substrate molecule is a peptide comprising phosphate groups, preferably phosphotyrosine or phosphoserine or phosphothreonine.

In a further embodiment, the detection entity is a peptide comprising phosphotyrosine and/or phosphoserine and/or phosphothreonine.

In another embodiment, the binding of the substrate molecule and detection entity to the binding partner involve ionic interactions. Preferably, the binding partner is selected from hard Lewis acid metal ions (e.g. In3+) or solids such as beads with ions on their surface e.g. IMAP beads.

In a third object, the invention relates to a kit for detecting a kinase or phosphatasee activity comprising a kinase and/or phosphatase activity substrate comprising a label having a detectable readout, a detection entity and a binding partner.

In a fourth object, the invention relates to a kit for detecting a kinase or phosphatasee activity comprising a kinase and/or phosphatase activity substrate comprising an aromatic group, a detection entity comprising a label having a detectable readout and a binding partner.

DETAILED DESCRIPTION OF THE INVENTION

The term "kinase activity" as used herein refers to a phosphorylation of a substrate by a kinase.

The term "phosphatase activity" as used herein refers to a dephosphorylation of a substrate by a phosphatase.

As used herein "fluorophore" refers to a component of a molecule which causes a molecule to be fluorescent. It is a functional group in a molecule which will absorb energy of a specific wavelength and re-emit energy at a different (but equally specific) wavelength.

The term "substrate molecule" as used herein refers to a molecule which is modified by a kinase or a phosphatase.

As used herein "detection entity" refers to a molecule which carries a label having a detectable readout, e.g. a fluorophore, or to a molecule which comprises an aromatic group, e.g. tyrosine, tryptophan, cGMP, cAMP derivative.

As used herein "binding partner" refers to an entity e.g. a molecule, which is capable of binding both, the phosphorylated substrate molecule and the detection entity.

The present invention describes a generic kinase/phosphatase assay which is based on the fact that fluorophores e.g. the oxazine dye MR121 or Atto 700, are quenched efficiently by molecules having an aromatic group, e.g. tryptophan which forms a non fluorescent ground state complex. The idea is to bring the entity having an aromatic group and the fluorophore in close proximity so that quenching by direct interaction of molecular orbitals—either by formation of a non-fluorescent ground state complex ("static quenching") or collisional quenching ("dynamic quenching")—can occur by binding the entity comprising the aromatic group and the fluorophore entity to a binding partner.

In comparison to existing quench assays, the advantage of such quench mechanism above dipole-dipole interaction like fluorescence resonance energy transfer (FRET) is that the interaction length is much shorter and quenching occurs only at very high, typically mM, local concentrations. For energy transfer a spectral overlap between a donor and an acceptor is required. This means a double labeling with two suitable molecules and a remaining absorbance of the donor emission if the acceptor is free in solution. Overall the hereby described more favorite quench system leads to less non-specific signals and a higher sensitivity.

Either the aromatic group or the fluorophore is part of the substrate peptide for the kinase or phosphatase activity investigated whereas the other is part of the detection entity. The binding partner binds the phosphorylated substrate peptide and the detection entity but not the unphosphorylated substrate peptide such that a kinase activity is measured by a decrease of fluorophore readout (fluorescence intensity) while a phosphatase activity causes an increase of fluorophore readout (fluorescence intensity). The fluorophore readout can e.g. be fluorescence intensity, fluorescence polarization, emission wavelength distribution or fluorescence lifetime.

The binding partner is an entity that can bind phosphate groups, preferably a hard Lewis acid metal ion (e.g. $In^{3+}$) or solids such as beads with ions on the surface (e.g. IMAP beads), or similar.

FIG. 1 shows the assay principle for an exemplary kinase substrate labeled with a suitable fluorophore (e.g. MR121 or Atto 700) and a detection entity containing a phosphate group and tryptophan. The substrate is phosphorylated by the kinase. When the biochemical reaction has finished the binding partner and the detection entity are added and the fluorescence measured. The more substrate is phosphorylated the less fluorescence is detected.

The robust and sensitive fluorescence readout and the simple and easy to use protocol makes the assay of the present invention also amenable for miniaturization of assay e.g. either in high density microtiter plates or for processing and readout in microfluidics systems.

SHORT DESCRIPTION OF THE FIGURES

FIG. 1 shows the general assay principle. A fluorescently labeled substrate (labeled with e.g. MR121 or Atto 700) is phosphorylated by the kinase. For the detection of phosphorylated substrate a binding partner and a detection entity containing a phosphate group and tryptophan are added to the substrate. Both, the phosphorylated substrate and the detection entity bind to the binding partner leading to a quenching of the fluorescence by tryptophan;

FIG. 2 shows the decrease of the MR121 (.) and Atto 700 (□) fluorescence in the presence of $InCl_3$. 20 nM MR121-CGpY or Atto 700-CGpY were mixed with 1 µM WGpY and different concentrations of $InCl_3$ and the MR121 and Atto 700 fluorescence was measured. The maximal quenching for the MR121 entity (20% of the initial MR121 fluorescence) is reached at 40 µM to 60 µM $InCl_3$ and for the Atto 700 entity (15% of the initial Atto 700 fluorescence) at 10 µM to 100 µM(b);

Figure 5:
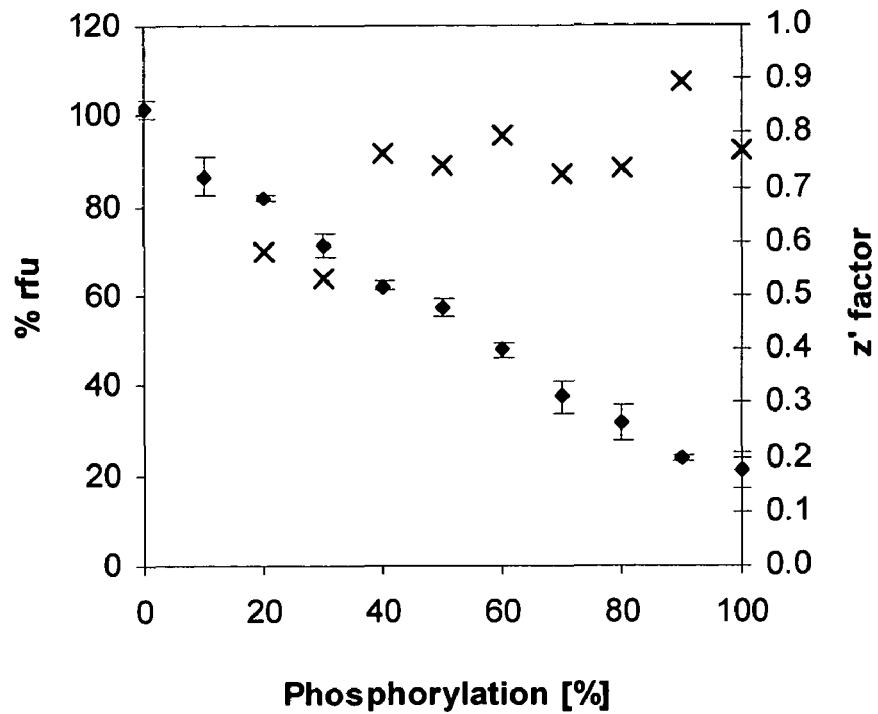

FIG. 5 shows 0% to 100% phosphorylation of the MR121-CGY peptide by mixing MR121-CGpY and MR121-CGY accordingly. 800 nM WGpY and 50 µM $InCl_3$ were used as detection entity and binding partner. The fluorescence intensity is decreasing with increasing phosphorylation to 20% of the initial fluorescence. The z' factor (crosses) is above 0.5 for >20% and above 0.7 for >40% phosphorylation and FIG. 6 shows a titration of WGpY (a) and IMAP beads (b) at a constant MR121-CGpY concentration (20 nM final concentration). For (a) the dilution of the IMAP beads was 1:1000, for (b) the final concentration of WGpY was 80 µM. The fluorescence intensity decreases with increasing WGpY concentration to 20% of the initial intensity at 80 µM WGpY. With a bead dilution 1:500 or 1:1000 the fluorescence intensity is equally quenched to 20% of the initial intensity, with higher bead dilutions the quenching is less efficient.

MATERIALS AND METHODS

All peptide substrates were synthesized with a purity of 95% from Biosyntan GmbH, Berlin. The reactive form of the fluorophore MR121 was provided by Roche Diagnostics, Penzberg and of Atto 700 by Atto-Tec GmbH, Siegen, Germany. Covalent coupling of MR121-maleimide and Atto 700-maleimide to the sulfhydryl group of the cysteine residue of the substrate peptide was done in house following a standard protocol for labeling with maleimide substrates and purified on an analytical HPLC (Merck Hitachi D-6000) using a C18 column (Marchery-Nagel, cc125/4, Nucleosil 100-5, protect 1).

Where $InCl_3$ (Sigma-Aldrich Co., Catalog No. 303440) was used as binding partner the reaction buffer was 100 mM NaAc/HAc (NaAc anhydrous, >99%, S8750, Sigma-Aldrich Co.) at pH 5.2. With IMAP beads as binding partner the buffer was 80% 1x IMAP binding buffer A and 20% 1x IMAP binding buffer B provided with the IMAP Kit (Molecular Devices, 1311 Orleans Drive, Sunnyvale, Calif. 94089). For all experiments 10 µl of the tryptophan entity, 10 µl of the fluorophore entity and 20 µl of the binding partner were mixed giving a total assay volume of 40 µl. Before reading the fluorescence intensity the plate was incubated for 60 minutes at RT in the dark.

All measurements were performed in 384 well microtiter plates (Comig B. V., Koolhovenlaan 12, 1119 Schiphol-Rijk, Netherlands, ref. # 3723, universal optics plate, clear, non-binding surface). All fluorescence intensity measurements were carried out by means of a plate::vision multimode reader (Evotec Technologies GmbH, Schnackenburgallee 114, 22525 Hamburg, Germany) equipped with a high pressure Xe arc lamp using an excitation filter at 630 nm (bandwidth 50 nm) and an emission filter at 695 nm (bandwidth 55 nm) for MR121 and an excitation filter at 655 nm (bandwidth 50 nm) and an emission filter at 710 nm (bandwidth 40 nm) for Atto 700. The fluorescent intensity was adjusted to about 60% of the maximal signal of the employed CCD camera by using attenuation filters and varying exposure times.

RESULTS

A. InCl$_3$ as Binding Partner

Figure 1:
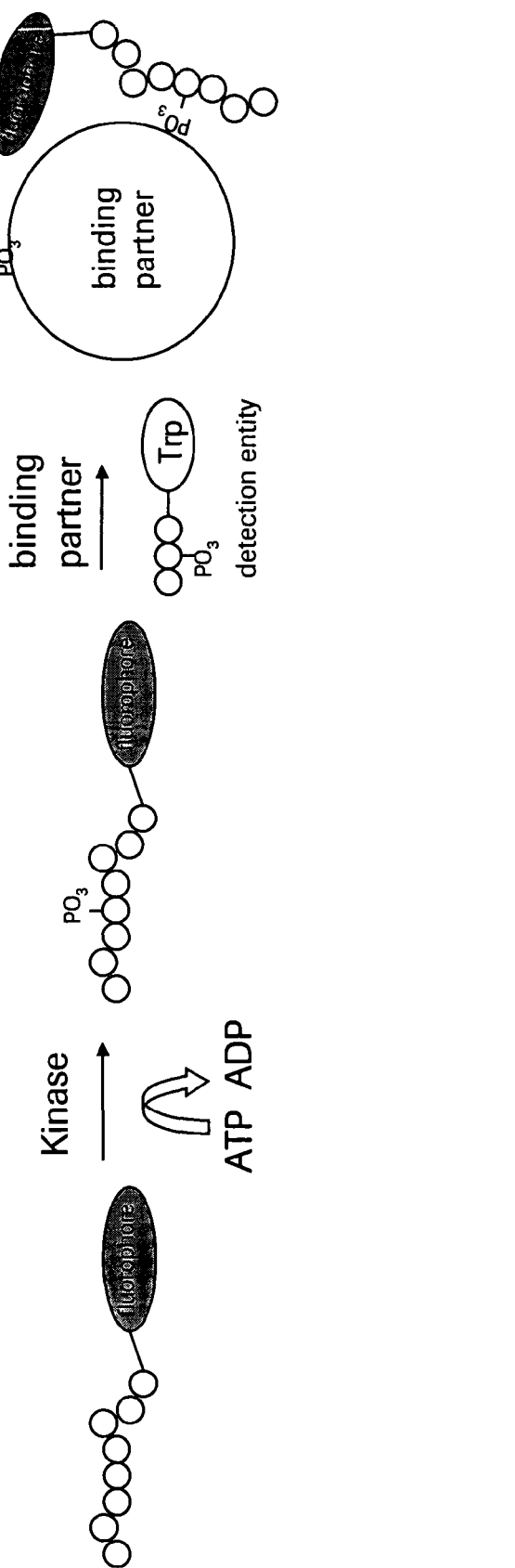
Figure 2A:
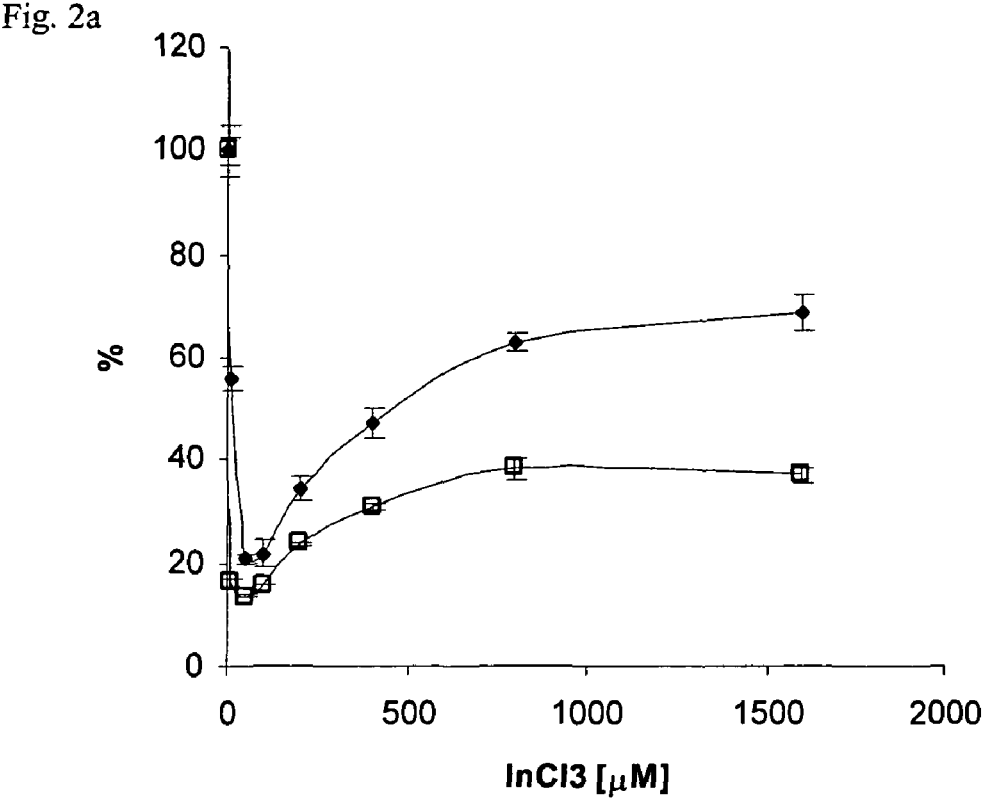
Figure 2B:
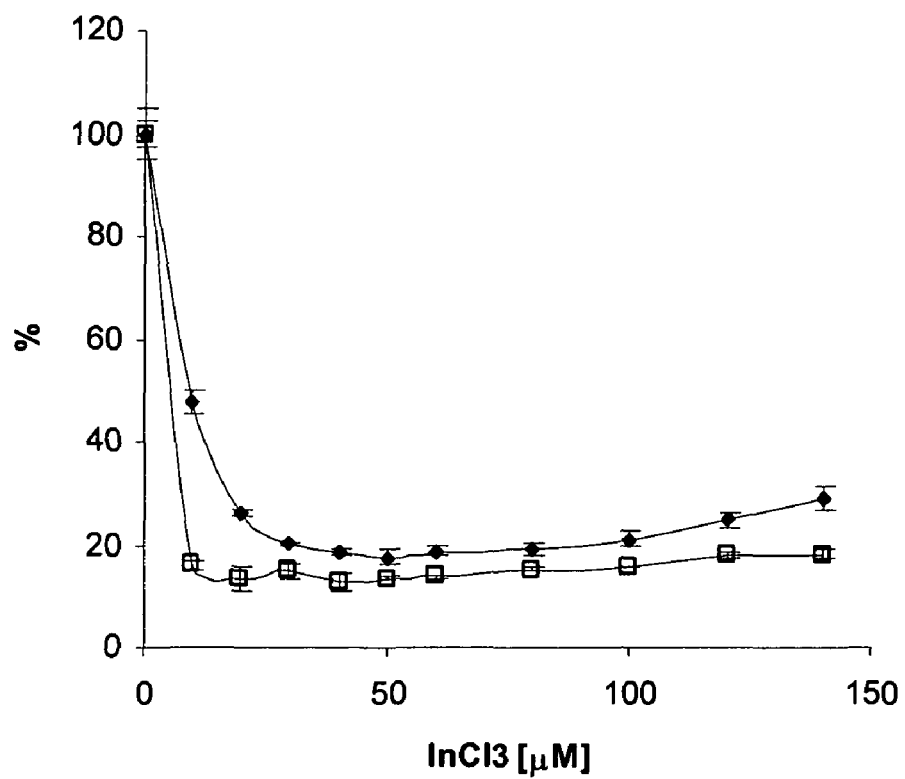
Figure 3A:
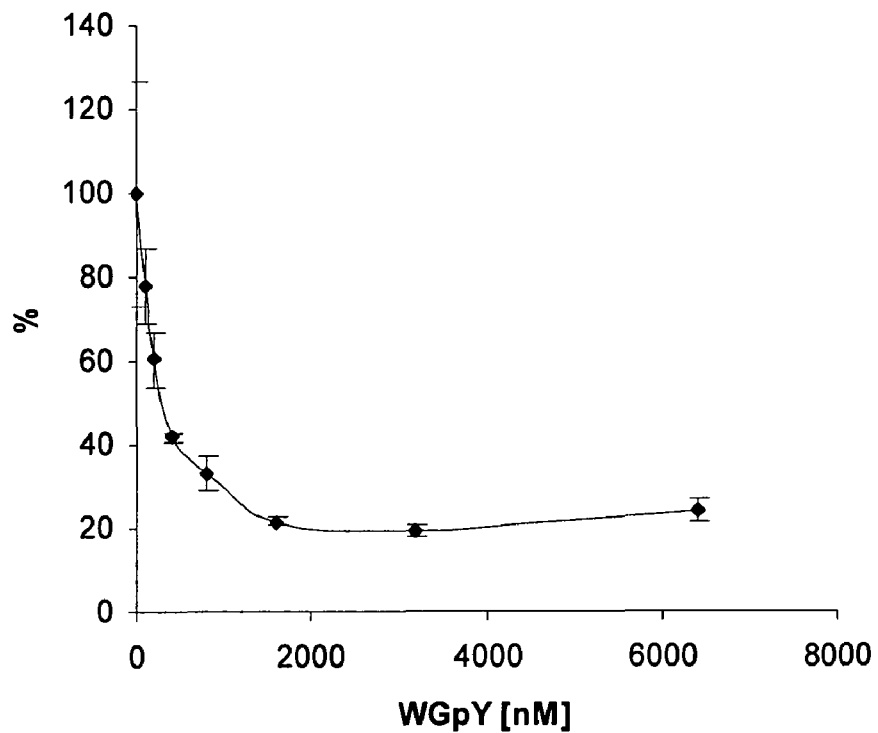
FIG. 3 shows a titration of WGpY at constant MR121-CGpY and $InCl_3$ concentrations (20 nM MR121-CGpY, 50 µM $InCl_3$). The maximal quenching is reached at 700 nM WGpY.
Figure 3B:
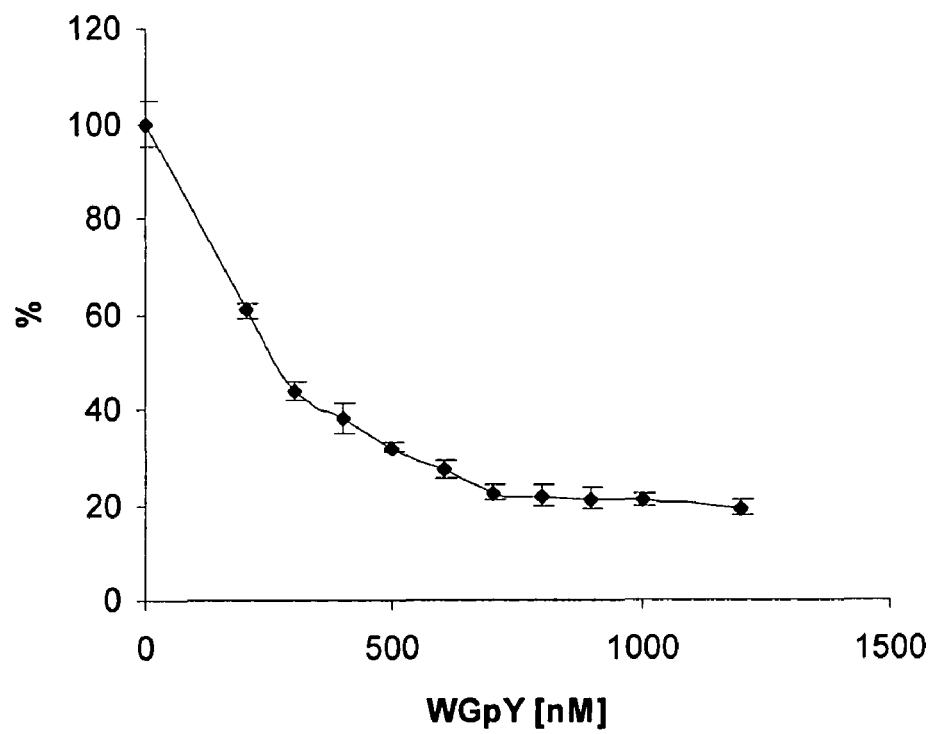
Figure 4:
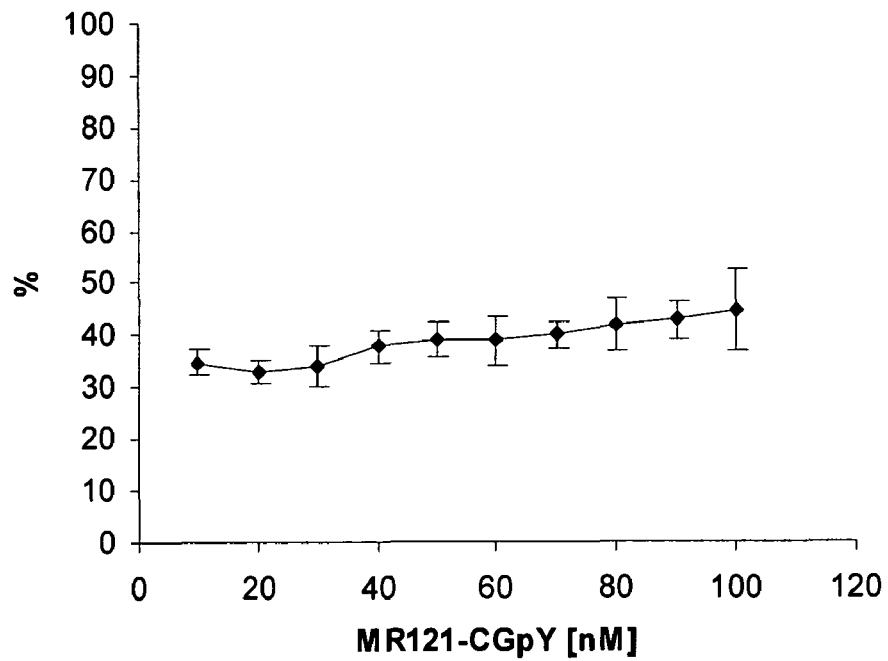
FIG. 4 shows a titration of MR121-CGpY at constant WGpY and $InCl_3$ concentrations (800 nM WGpY, 50 µM $InCl_3$)

PO$_3^{2-}$ is a hard Lewis base and forms complexes with hard Lewis acid metal ions. The oxygens of the phosphate group can coordinate to a single metal ion or crosslink some metal ions to form a polymer type complex. Hard Lewis acid metal ions can thus be used as binding partner to bring the fluorophore entity and the tryptophan entity in close proximity to form a non fluorescent ground state complex. For proof of principle short peptides were used as fluorophore and tryptophan entity containing phosphotyrosine, tyrosine and/or tryptophan, respectively. As fluorophore entity phosphorylated and unphosphorylated peptides of the sequence Cys-Gly-Tyr labeled with MR121 and Atto 700 at the Cys residue were used (MR121-CGY, MR121-CGpY, Atto 700-CGY and Atto 700-CGpY hereafter) and the detection entity was a peptide of the sequence Trp-Gly-pTyr where pTyr is phosphorylated tyrosine (WGpY hereafter). FIG. 2 shows a titration of InCl$_3$ as binding partner at fixed MR121-CGpY or Atto 700-CGpY and WGpY concentrations (final concentrations: MR121-CGpY 20 nM, Atto 700-CGpY 20 nM, WGpY 1 µM). The fluorescence emission of MR121 is quenched to 20% of the initial MR121 fluorescence (fluorescence in absence of InCl$_3$) in presence of 50 µM to 100 µM InCl$_3$. With higher concentrations of InCl$_3$ the MR121 fluorescence increases to 70% of the initial MR121 fluorescence (FIG. 2a) indicating that the MR121 entity and the tryptophan entity are not bound to the same In-complex anymore. FIG. 2b shows a zoom-in from 10 µM to 140 µM InCl$_3$ to find the optimal InCl$_3$ concentration. The Atto 700 fluorescence is quenched to 15% of its initial fluorescence already at 10 µM InCl$_3$. Similar to the MR121 entity the Atto 700 fluorescence increases again with higher InCl$_3$ concentrations. All subsequent experiments were done with 50 µM InCl3 and the MR121 entity. In a next step the WGpY concentration was optimized. FIG. 3 shows a titration of WGpY with 20 nM MR121-CGpY (final conc.) and 50 µM InCl$_3$ (final conc.). At 700 nM WGpY the fluorescence intensity reaches its minimum (FIG. 3b). With higher concentrations of MR121-CGpY the fluorescence intensity increases slightly (from 30% of the initial intensity at 20 nM to 45% at 100 nM) (FIG. 4). In a final experiment the fluorescence intensity of 0% to 100% substrate phosphorylation was measured (FIG. 5). MR121-CGpY and MR121-CGY were mixed accordingly to give 20 nM MR121-CG(p)Y final concentration with increasing phosphorylated peptide. 800 nM WGpY were used as detection entity and 50 µM InCl$_3$ as binding partner. The fluorescence intensity decreases linearly with increasing phosphorylation from 100% to 20% of the initial intensity. As a measure of the quality of the assay the z' factor was calculated. From 20% phosphorylation on the z' factor is above 0.5 (theoretical max. value 1) and from 40% on above 0.7.

B. IMAP Beads as Binding Partner

Figure 6A:
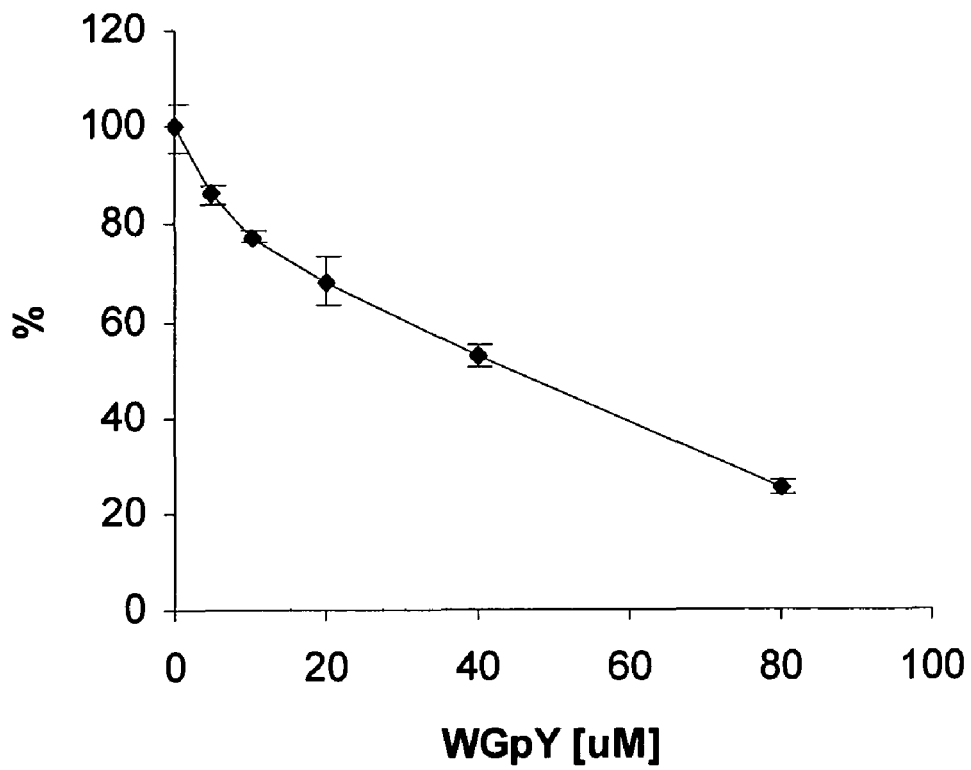
Figure 6B:
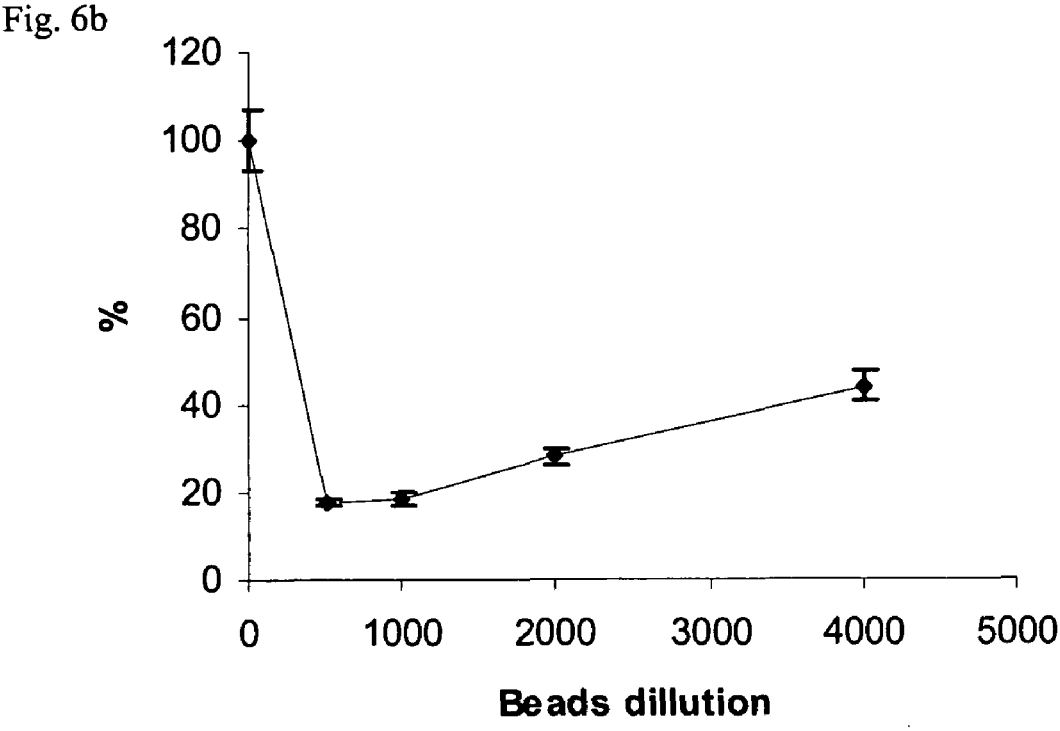

For the experiments with IMAP beads as binding partner the same short model peptides were uses a MR121 and tryptophan entity as for InCl$_3$ as binding partner. With a diameter of ~100 nm the IMAP beads are significantly larger than In3$^+$ions and thus a 4-fold higher concentration of the WGpY is necessary to achieve a good quenching of the MR121 entity. Although the IMAP beads are not working as well as the InCl$_3$ in a sense that higher reagent concentrations are required, the novel and sensitive assay allows the system to be used as a binding partner. FIG. 6a shows the decrease in intensity of 20 nM MR121-CGpY with increasing WGpY concentration with IMAP beads diluted 1:1000. At 80 µM WGpY the MR121 fluorescence is quenched to 20% of the initial intensity. At a constant concentration of 80 µM WGpY higher dilutions of the IMAP beads do not lead to a better quenching (FIG. 6b), the optimal dilution lies between 1:500 and 1:1000.

CONCLUSIONS

With the examples described here we demonstrate that kinase or phosphatase activity can be detected by measuring a decrease (kinase) or increase (phosphatase) of the fluorescence intensity of a suitable fluorophore (e.g. MR121, Atto 700). The quenching of the fluorophore by tryptophan being either static quenching by formation of a non-fluorescent ground state complex or collisional quenching is a short range interaction what assures that it occurs only if the fluorophore entity and the tryptophan entity are bound to the binding partner. This is on contrary to a regular FRET measurement where there may be absorption of the donor emission by the acceptor also without binding to the binding partner at high concentrations of the fluorophores. Similar to FP measurements there is only one label needed for the quenching assay described here but while in FP two readouts are necessary the measure of the quenching of the fluorescence requires only a single readout. The robust and sensitive fluorescence readout and the simply and easy to use protocol makes the assay also amenable for e.g. either in high density microtiter plates or for processing and readout in a microfluidics system. Because the fluorophores used, e.g. MR121 and Atto 700, are excited in the red with a fluorescence emission in the near infrared it has proven to be very sensitive and shows minimal interference with auto fluorescence of e.g. compounds, biological material and plastic. The three components—the fluorophore entity, the tryptophan entity and the binding partner—can be titrated against each other to find optimal conditions for each assay providing unique flexibility.

While there are shown and described presently preferred embodiments of the invention, it is to be distinctly understood that the invention is not limited thereto but may be otherwise variously embodied and practiced within the scope of the following claims.

The invention claimed is:

1. A method for detecting a kinase activity or phosphatase activity comprising the steps:
   a) incubating a kinase or phosphatase activity sample with a kinase or phosphatase substrate molecule comprising a fluorophore having a detectable readout,
   b) incubating the mixture of step a) with a detection entity, comprising an aromatic group, and a binding partner, wherein the phosphorylated substrate molecule and the detection entity are capable of binding to the binding partner and the binding of the substrate molecule and the detection entity to the binding partner lead to an altered readout of the fluorophore wherein the binding of the substrate molecule and the detection entity to the binding partner involves ionic interactions, and c) measuring the readout of the fluorophore in the mixture of step b), wherein an altered readout of the fluorophore compared to a blank is indicative for the presence of a kinase or phosphatase activity in the sample, wherein the fluorophore is selected from the group consisting of Fluorescein, Rhodamine B, TMR, ATTO 590, ATTO 655, ATTO 680, Atto 700, MR 121, Bodipy 630/650 and Bodipy FL;

and further wherein the aromatic group is selected from the group consisting of the amino acids tryptophan, tyrosine and phenylalanine.

2. A method for detecting a kinase activity or phosphatase activity comprising the steps:

a) incubating a kinase or phosphatase activity sample with a substrate molecule comprising an aromatic group, b) incubating the mixture of step a) with a detection entity, comprising a fluorophore having a detectable readout, and a binding partner, wherein the phosphorylated substrate molecule and the detection entity can bind to the binding partner and the binding of the substrate molecule and the detection entity to the binding partner lead to an altered readout of the fluorophore wherein the binding of the substrate molecule and the detection entity to the binding partner involves ionic interactions, and c) measuring the readout of the fluorophore in the mixture of step b), wherein an altered readout of the fluorophore compared to a blank is indicative for the presence of a kinase or phosphatase activity in the sample wherein the fluorophore is selected from the group consisting of Fluorescein, Rhodamine B, TMR, ATTO 590, ATTO 655, ATTO 680, Atto 700, MR 121, Bodipy 630/650 and Bodipy FL, and further wherein the aromatic group is selected from the group consisting of the amino acids tryptophan, tyrosine and phenylalanine.

3. The method of claim 1, wherein the fluorophore is MR 121 or Atto 700.

4. The method of claim 1, wherein the detection entity is a peptide comprising phosphotyrosine and/or phosphoserine and/or phosphorthreonine.

5. The method of claim 1, wherein the substrate molecule is a peptide comprising at least a tyrosine and/or serine and/or threonine.

6. The method of claim 5, wherein the method is for detecting a tyrosine kinase activity and the substrate peptide comprises at least a tyrosine.

7. The method of claim 5, wherein the method is for detecting a serine kinase activity and the substrate peptide comprises at least a serine.

8. The method of claim 5, wherein the method is for detecting threonine kinase activity and the substrate peptide comprises at least a threonine.

9. The method of claim 5, wherein the method is for detecting a phosphatase activity and the substrate molecule is a peptide comprising phosphotyrosine or phosphoserine or phosphothreonine.

10. The method of claim 1, wherein the fluorophore readout is fluorescence intensity.

11. A kit for detecting a kinase or phosphatase activity according to the method of claim 1 comprising a kinase and/or phosphatase activity substrate comprising a fluorophore having a detectable readout, a detection entity and a binding partner.

12. A kit for detecting a kinase or phosphatasee activity according to the method of claim 2 comprising a kinase and/or phosphatase activity substrate comprising an aromatic group, a detection entity comprising a fluorophore having a detectable readout and a binding partner.

13. The method of claim 2, wherein the binding of the substrate molecule and the detection entity to the binding partner involve ionic interactions.

14. The method of claim 2, wherein the detection entity is a peptide comprising phosphotyrosine and/or phosphoserine and/or phosphothreonine.

15. The method of claim 2, wherein the substrate molecule is a peptide comprising at least a tyrosine and/or serine and/or threonine.

16. The method of claim 15, wherein the method is for detecting a tyrosine kinase activity and the substrate peptide comprises at least a tyrosine.

17. The method of claim 2, wherein the fluorophore is selected from the group consisting of ATTO 590, ATTO 655, ATTO 680, Atto 700 and MR 121, and further wherein the aromatic group is tryptophan.

18. The method of claim 15, wherein the method is for detecting threonine kinase activity and the substrate peptide comprises at least a threonine.

19. The method of claim 2, wherein the method is for detecting a phosphatase activity and the substrate molecule is a peptide comprising phosphotyrosine or phosphoserine or phosphothreonine.

20. The method of claim 2, wherein the fluorophore readout is fluorescence intensity.

21. The method of claim 3, wherein the aromatic group is tryptophan.

22. The method of claim 15, wherein the method is for detecting a serine kinase activity and the substrate peptide comprises at least a serine.

* * * * *